PROCESS FOR IMMOBILIZATION OF GLUCOAMYLASE

This application is a continuation of U.S. application Ser. No. 541,432, filed Oct. 13, 1983, now abandoned.

This invention relates to the preparation of an immobilized glucoamylase enzyme composition, more particularly it is concerned with a process for the immobilization of glucoamylase enzyme on xerogels.

From the organic substances produced in the photosynthesis of plant organisms starch is a highly important industrial raw material. Recently enzymatic transformations of starch and the industrial scale realization of the said procedures have come into prominence. One of the most important transformations of starch is its hydrolytical conversion into glucose which is generally carried out by treating a starch partially hydrolysed by means of an acid or α-amylase with a glucoamylase enzyme. The said glucoamylase enzyme splits off the glucose units from the non-reducing end of the dextrines. When using dissolved glucoamylase only batchwise or semi-continuous methods are applicable and no economical process is known for the separation of the dissolved enzyme in active form at the end of the reaction. For this reason already at the end of the 1960 years attempts were made for the immobilization of the enzyme by binding the enzyme to diethylaminoethyl cellulose with the aid of 2-amino-4,6-dichloro-s-triazine (Biotechn. Bioeng. 11, 349 (1969)). In the past years other methods have also become known. According to the articles published in Biotechn. Bioeng. 12, 85 (1970), Biotechn. Bioeng. 2273 (1981) and Ann Technol. Agric. 27, 469 (1978) the enzyme can be effectively immobilized through ionic bonds on a DEAE-cellulose, methyl-methacrylate-2-dimethylaminoethyl-methacrylate copolymer or Amberlite IRA 93, respectively, as a carrier. The immobilization on a glass or silica carrier is disclosed in the following prior art reference: Biotech. Bioeng. Symp. 3, 241 (1972); Biotech. Bioeng. 15, 483 (1973); Biotech. Bioeng. 18, 253 (1976); Prikl. Biohim. Mikrobiol. 15, 744 (1979); Enzyme Microb. Technol. 1, 197 (1979); Biotech. Bioeng. 23, 2083 (1981); Enzyme Microb. Technol. 4, 89 (1982) and Enzyme Microb. Technol. 4, 107 (1982), U.S. Pat. No. 3,783,101.

The immobilization on polysaccharide (mainly cellulose) carriers is set forth in Biochim. Biophys. Acta 276, 339 (1972); Biochim. Biophys. Acta 341, 457 (1974); Acta biol. med. germ. 36, 179 (1977); Starch-Stärke 30, 414 (1978); Prikl. Biochim. Mikrobiol. 14, 548 (1978) and Collection Czechoslov. Chem. Commun. 45, 2847 (1980) and U.S. Pat. Nos. 3,810,821, 4,063,017, 4,090,022 and 4,048,416. The following references relate to the use of synthetic polymers for the immobilization of glucoamylase: J. Jap. Soc. Starch Sci. 24, 1 (1977); Int. J. Biochem. 8, 501 (1977); Biotech. Bioeng. 20, 1319 (1978) and Enzyme Microb. Technol. 4, 143 (1982) and U.S. Pat. No. 4,066,504.

The known methods comprise the following drawbacks:
use of special, which are not readily available carriers;
use of complicated coupling methods;
lower stability of the immobilized enzyme.

The object of the present invention is to eliminate the disadvantages of the known methods and to provide a process for the preparation of an immobilized glucoamylase composition which produces an enzyme composition suitable for prolonged application and in which the enzyme is bound onto a carrier which is chemically inert, is resistant to the effect of microorganisms, possesses favourable mechanical properties and ensures a large flow velocity. A further object of the invention is to provide a process wherein the enzyme to be immobilized is bound to the carrier under mild chemical and physical conditions.

It has been found that polymers which are produced from acrylic and/or methacrylic acid or acrylamide and/or methacrylamide, or N-aminoethyl-acrylic amide and/or N-aminoethyl-methacrylic amide monomers by means of a cross-linking agent of the acrylic or allylic type (e.g. N,N'-methylene-bis-acrylic amide, ethylene diacrylate or N,N'-diallyl-tartaric amide) and which contain at least 1.0 m.equiv./g—preferably 2–7 m.equiv./g—of —COOH or —NH$_2$ functional group, fully comply with the above requirements.

When a carrier comprising primary amino groups is used, the carboxy groups of the aspartic or glutamic side chain of the enzyme are converted by treatment with a carbodiimide into a O-acyl-isourea derivative which then reacts with the amino groups of the carrier. When polymeric carriers comprising functional carboxy groups are used, the said carboxy groups are activated by treatment with a carbodiimide being known per se and the thus-treated polymeric carrier is suitable for binding the glucoamylase enzyme. The use of carbodiimides as activator is advantageous because the said activation reaction can be carried out under mild conditions (0°–4° C., pH 6.0–8.0).

According to the present invention there is provided a process for the preparation of an immobilized glucoamylase composition which comprises (a) treating a glucoamylase enzyme with a carbodiimide compound being soluble in water or soluble in an organic solvent at a temperature below 0° C. and applying the thus-treated enzyme in a solution having a pH value of 4.5–9.0 onto a polymer which is produced from a N-aminoethyl-acrylic amide and/or N-aminoethyl-methacrylic amide, or acrylic amide and/or methacrylic amide monomer by means of a cross-linking agent of the acrylic or allylic type and which comprises at least 1.0 m.equiv./g of —NH$_2$ groups; or (b) treating a polymer which is produced from an acrylic acid and/or methacrylic acid or acrylic amide and/or methacrylic amide monomer by means of cross linking agent of the acrylic or allylic type and which comprises at least 1.0 m.equiv./g of functional —COOH groups with a carbodiimide compound soluble in water or soluble in an organic solvent at a temperature below 0° C. and applying onto the thus-treated carrier a glucoamylase enzyme in a solution having a pH value between 4.5 and 9.0.

In both cases (a) and (b) the product obtained is filtered, washed and, if desired, dried.

As the polymer, preferably, an acrylic amide-N,N'-methylene-bis-acrylic amide acrylic acid copolymer can be used which has an exclusion molecular weight limit of 100 000 daltons (Acrylex C-100, X-200, C-300). Alternatively an acrylic amide-N,N'-methylene-bis-acrylic amide-N-aminoethyl-acrylic amide copolymer (Acrylex A) can be used as well.

According to the process of the present invention any glucoamylase enzyme of whatever origin and separated by any known method can be used.

As activating carbodiimide compound e.g. N-cyclohexyl-N'-[2-(4-morpholinyl)-ethyl]-carbodiimidesalt-free with distilled water and subjected to lyophilization. Thus 0.7 g of immobilized glucoamylase is obtained. Activity: 0.75 g.

EXAMPLE 6

0.5 g of Acrylex C-100 xerogel (binding capacity—i.e. —COOH content—6.2 m.equiv./g, particle size 100–320 μm) is suspended in 50 ml of a 0.1 molar sodium acetate buffer (pH 6.0) whereupon 1 g of N-cyclohexyl-N'-[2-(4-morpholinyl)-ethyl]-carbodiimide-methyl-p-toluene-sulfonate is added on an icecold water-bath under constant stirring. The reaction mixture is stirred for 10 minutes, whereupon 1.7 ml of a glucoamylase solution (117.7 mg/ml) are added and the pH value of the reaction mixture is adjusted to 6.0. At 0°–4° C. the complete reaction time amounts to 48 hours and during this period the suspension is stirred twice for 6 hours each. The pH is controlled at the beginning every half an hour and later once an hour and is if necessary re-adjusted. After the reaction has been completed, the gel is removed by filtration and washed three times with 50 ml of a 0.1 molar sodium acetate buffer each (pH 6.0), three times with 50 ml of a 1.0 molar sodium acetate buffer comprising 1.0 mole of sodium chloride each (pH 6.0) and three times with 50 ml of a 0.1 molar sodium acetate buffer each (pH 6.0). The gel is finally washed salt-free with distilled water and subjected to lyophilization. Thus 0.7 g of immobilized glucoamylase is obtained. Activity: 1.35 g of glucose are set free/hour/g xerogel.

EXAMPLE 7

0.5 g of Acrylex C-100 xerogel (binding capacity—i.e.—COOH content—6.2 m.equiv./g, particle size 100–320 μm) is suspended in 50 ml of a 0.1 molar sodium acetate buffer (pH 7.0), whereupon 1 g of N-cyclohexyl-N'-[2-(4-morpholinyl)-ethyl]-carbodiimide-methyl-p-toluene-sulfonate is added on an icecold water-bath under constant stirring. The reaction mixture is stirred for 10 minutes, whereupon 1.7 ml of a glucoamylase solution (117.7 mg/ml) are added and the pH value of the reaction mixture is adjusted to 7.0. At 0°–4° C. the complete reaction time amounts to 48 hours and during this period the suspension is stirred twice for 6 hours each. The pH is controlled at the beginning every half an hour and later once an hour and is, if necessary, re-adjusted. The reaction having been completed the gel is removed by filtration and washed three times with 50 ml of a 0.1 molar sodium acetate buffer each (pH 7.0), three times with 50 ml of a 1.0 molar sodium acetate buffer comprising 1.0 mole of sodium chloride each (pH 7.0) and three times with 50 ml of a 0.1 molar sodium acetate buffer each (pH 7.0). The gel is finally washed salt-free with distilled water and subjected to lyophilization. Thus 0.6 g of immobilized glucoamylase is obtained. Activity: 3.0 g. of glucose is set free/hour/g xerogel.

EXAMPLE 8

0.5 g of Acrylex C-100 xerogel (binding capacity—i.e. —COOH content—6.2 m.equiv./g, particle size 100–320 μm) is suspended in 50 ml of a 0.1 molar sodium acetate buffer (pH 7.5), whereupon 1 g of N-cyclohexyl-N'-[2-(4-morpholinyl)-ethyl]-carbodiimide-methyl-p-toluene-sulfonate is added on an icecold water-bath under constant stirring. The reaction mixture is stirred for 10 minutes, whereupon 1.7 ml of a glucoamylase solution (117.7 mg/ml) are added and the pH value of the reaction mixture is adjusted to 7.5. At 0°–4° C. the complete reaction time amounts to 48 hours and during this period the suspension is stirred twice for 6 hours each. The pH is controlled at the beginning every half an hour and later once an hour and is, if necessary, re-adjusted. The reaction having been completed the gel is removed by filtration and washed three times with 50 ml of a 0.1 molar sodium acetate buffer each (pH 7.5), three times with 50 ml of a 1.0 molar sodium acetate buffer comprising 1.0 mole of sodium chloride each (pH 7.5) and three times with 50 ml of a 0.1 molar sodium acetate buffer each (pH 7.5). The gel is finally washed salt-free with distilled water and subjected to lyophilization. Thus 0.75 g of immobilized glucoamylase is obtained. Activity: 5.7 g of glucose is set free/hour/g xerogel.

EXAMPLE 9

0.5 g of Acrylex C-100 xerogel (binding capacity—i.e. —COOH content—6.2 m.equiv./g, particle size 100–320 μm) is suspended in 50 ml of a 0.1 molar sodium acetate buffer (pH 8.0), whereupon 1 g of N-cyclohexyl-N'-[2-(4-morpholinyl)-ethyl]-carbodiimide-methyl-p-toluene-sulfonate is added on an icecold water-bath under constant stirring. The reaction mixture is stirred for 10 minutes, whereupon 1.7 ml of a glucoamylase solution (117.7 mg/ml) are added and the pH value of the reaction mixture is adjusted to 8.0. At 0°–4° C. the complete reaction time amounts to 48 hours and during this period the suspension is stirred twice for 6 hours each. The pH is controlled at the beginning every half an hour and later once an hour and is, if necessary, re-adjusted. The reaction having been completed the gel is removed by filtration and washed three times with 50 ml of a 0.1 molar sodium acetate buffer each (pH 8.0), three times with 50 ml of a 1.0 molar sodium acetate buffer comprising 1.0 mole of sodium chloride each (pH 8.0) and three times with 50 ml of a 0.1 molar sodium acetate buffer each (pH 8.0). The gel is finally washed salt-free with distilled water and subjected to lyophilization. Thus 0.65 g of immobilized glucoamylase is obtained. Activity: 3.9 g of glucose is set free/hour/g xerogel.

EXAMPLE 10

0.5 g of Acrylex C-100 xerogel (binding capacity—i.e. —COOH content—6.2 m.equiv/g, particle size 100–320 μm) is suspended in 50 ml of a 0.1 molar sodium acetate buffer (pH 8.5), whereupon 1 g of N-cyclohexyl-N'-[2-(4-morpholinyl)-ethyl]-carbodiimide-methyl-p-toluene-sulfonate is added on an icecold water-bath under constant stirring. The reaction mixture is stirred for 10 minutes, whereupon 1.7 ml of a glucoamylase solution (117.7 mg/ml) are added and the pH value of the reaction mixture is adjusted to 8.5. At 0°–4° C. the complete reaction time amounts to 48 hours and during this period the suspension is stirred twice for 6 hours each. The pH is controlled at the beginning every half an hour and later once an hour and is, if necessary, re-adjusted. The reaction having been completed the gel is removed by filtration and washed three times with 50 ml of a 0.1 molar sodium acetate buffer each (pH 8.5), three times with 50 ml of a 1.0 molar sodium acetate buffer comprising 1.0 mole of sodium chloride each (pH 8.5) and three times with 50 ml of a 0.1 molar sodium acetate buffer each (pH 8.5). The gel is finally washed salt-free with distilled water and subjected to lyophilization. Thus 0.7 g of immobilized glucoamylase is obtained. Activity: 2.2 g of glucose is set free/hour/g xerogel.

EXAMPLE 11

0.5 g of Acrylex C-100 xerogel (binding capacity—i.e. —COOH content—6.2 m.equiv./g, particle size 100–320 μm) is suspended in 50 ml of a 0.1 molar sodium acetate buffer (pH 9.0), whereupon 1 g of N-cyclohexyl-N'-[2-(4-morpholinyl)-ethyl]-carbodiimide-methyl-p-toluene-sulfonate is added on an icecold water-bath under constant stirring. The reaction mixture is stirred for 10 minutes, whereupon 1.7 ml of a glucoamylase solution (117.7 mg/ml) are added and the pH value of the reaction mixture is adjusted to 9.0. At 0°–4° C. the complete reaction time amounts to 48 hours and during this period the suspension is stirred twice for 6 hours each. The pH is controlled at the beginning every half an hour and later once an hour and is, if necessary, re-adjusted. The reaction having been completed the gel is removed by filtration and washed three times with 50 ml of a 0.1 molar sodium acetate buffer each (pH 9.0), three times with 50 ml of a 1.0 molar sodium acetate buffer comprising 1.0 mole of sodium chloride each (pH 9.0) and three times with 50 ml of a 0.1 molar sodium acetate buffer each (pH 9.0). The gel is finally washed salt-free with distilled water and subjected to lyophilization. Thus 0.8 g of immobilized glucoamylase is obtained. Activity: 1.25 g of glucose are set free/hour/g xerogel.

EXAMPLE 12

0.5 g of Acrylex C-100 xerogel (binding capacity—i.e. —COOH content—6.2 m.equiv./g, particle size 100–320 μm) is suspended in 50 ml of a 0.1 molar potassium phosphate buffer (pH 7.5), whereupon 0.5 g of N-cyclohexyl-N'-[2-(4-morpholinyl)-ethyl]-carbodiimide-methyl-p-toluene sulfonate is added in an icecold water-bath under constant stirring. The reaction mixture is stirred for 10 minutes whereupon 2 ml of a glucoamylase solution (125 mg/ml) are added and the pH of the reaction mixture is adjusted to 7.5. At 0°–4° C. the complete reaction time amounts to 48 hours during this period the suspension is stirred twice for 6 hours each. At the beginning of the reaction the pH is controlled every half an hour and later once an hour and is adjusted, if necessary. The reaction having been completed the gel is separated by filtration and washed three times with 50 ml of a 0.1 molar potassium phosphate buffer each (pH 7.5), three times with 50 ml of a 0.1 molar potassium phosphate buffer comprising 1 mole of sodium chloride each (pH 7.5) and three times with 50 ml of a 0.1 molar potassium phosphate buffer each (pH 7.5). The gel is finally washed salt-free with distilled water and subjected to lyophilization. Thus 0.65 g of immobilized glucoamylase are obtained. Activity: 1.32 g of glucose are set free/hour/g xerogel.

EXAMPLE 13

0.5 g of Acrylex C-100 xerogel (binding capacity—i.e. —COOH content—6.2 m.equiv./g, particle size 100–320 μm) is suspended in 50 ml of a 0.1 molar potassium phosphate buffer (pH 7.5), whereupon 0.5 g of N-cyclohexyl-N'-[2-(4-morpholinyl)-ethyl]-carbodiimide-methyl-p-toluene sulfonate is added in an icecold water-bath under constant stirring. The reaction mixture is stirred for 10 minutes whereupon 1 ml of a glucoamylase solution (125 mg/ml) are added and the pH of the reaction mixture is adjusted to 7.5. At 0°–4° C. the complete reaction time amounts to 48 hours and during this period the suspension is stirred twice for 6 hours each. At the beginning of the reaction the pH is controlled every half an hour and later once an hour and is adjusted, if necessary. The reaction having been completed the gel is separated by filtration and washed three times with 50 ml of a 0.1 molar potassium phosphate buffer each (pH 7.5), three times with 50 ml of a 0.1 molar potassium phosphate buffer comprising 1 mole of sodium chloride each (pH 7.5) and three times with 50 ml of a 0.1 molar potassium phosphate buffer each (pH 7.5). The gel is finally washed salt-free with distilled water and subjected to lyophilization. Thus 0.6 g of immobilized glucoamylase are obtained. Activity: 2.08 g of glucose are set free/hour/g xerogel.

EXAMPLE 14

0.5 g of Acrylex C-100 xerogel (binding capacity—i.e. —COOH content—6.2 m.equiv./g, particle size 100–320 μm) is suspended in 50 ml of a 0.1 molar potassium phosphate buffer (pH 7.5), wherein 1 g of N-cyclohexyl-N'-[2-(4-morpholinyl)-ethyl]-carbodiimide-methly-p-toluene sulfonate is added in an icecold water-bath under constant stirring. The reaction mixture is stirred for 10 minutes whereupon 1.7 ml of a glucoamylase solution (117.7 mg/ml) are added and the pH of the reaction mixture is adjusted to 7.5. At 0°–4° C. the complete reaction time amounts to 48 hours and during this period the suspension is stirred twice for 6 hours each. At the beginning of the reaction the pH is controlled every half an hour and later once an hour and is adjusted, if necessary. The reaction having been completed the gel is separated by filtration and washed three times with 50 ml of a 0.1 molar potassium phosphate buffer each (pH 7.5), three times with 50 ml of a 0.1 molar potassium phosphate buffer comprising 1 mole of sodium chloride each (pH 7.5) and three times with 50 ml of a 0.1 molar potassium phosphate buffer each (pH 7.5). The gel is finally washed salt-free with distilled water and subjected to lyophilization. Thus 0.7 g of immobilized glucoamylase are obtained. Activity: 4.7 g of glucose are set free/hour/g xerogel.

TABLE 2

Effect of the pH on the immobilization of glucoamelyase enzyme on Acrylex C-100 carrier

| pH of the reaction mixture | Immobilized activity, (%) | Activity recovered in dissolved form (%) | Loss of activity (%) | Activity of the product /unit/g xerogel |
|---|---|---|---|---|
| 4.5 | 0.4 | 56.5 | 43.1 | 0.85 |
| 5.0 | 0.5 | 54.8 | 44.7 | 0.75 |
| 6.0 | 0.7 | 52.2 | 47.1 | 1.35 |
| 7.0 | 1.3 | 49.1 | 49.6 | 3.00 |
| 7.5 | 4.3 | 45.3 | 50.4 | 5.70 |
| 8.0 | 2.5 | 41.0 | 56.5 | 3.90 |
| 8.5 | 1.1 | 44.0 | 54.9 | 2.20 |

TABLE 2-continued

Effect of the pH on the immobilization of glucoamelyase enzyme on Acrylex C-100 carrier

| pH of the reaction mixture | Immobilized activity, (%) | Activity recovered in dissolved form (%) | Loss of activity (%) | Activity of the product /unit/g xerogel |
| --- | --- | --- | --- | --- |
| 9.0 | 0.7 | 42.0 | 57.3 | 1.25 |

TABLE 3

Effect of the composition of the reaction mixture on the immobilization of glucoamylase enzyme on an Acrylex C-100 carrier

| Composition of the reaction mixture | | | | | | |
| --- | --- | --- | --- | --- | --- | --- |
| [1]AC-100 (mg) | [2]CMC (mg) | [3]GA (mg) | Immobilized activity (%) | Activity recovered in dissolved form (%) | Loss of activity (%) | Activity of the product /unit/g xerogel |
| 500 | 500 | 125 | 0.6 | 75.7 | 24.3 | 1.32 |
| 500 | 500 | 250 | 0.5 | 56.1 | 43.4 | 2.08 |
| 500 | 1000 | 200 | 2.3 | 45.2 | 52.5 | 4.70 |

[1] = AC-100, Acrylex C-100
[2] = CMC, N—cyclohexyl-N'—[2-(4-morpholinyl)-ethyl]-carbodiimide-methyl-p-toluene-sulfonate
[3] = GA, glucoamylase.

EXAMPLE 15

0.5 g of Acrylex C-200 xerogel (binding capacity—i.e. —COOH content—7.49 m.equiv/g, particle size 120–320 μm) is suspended in 100 ml of a 0.1 molar potassium phosphate buffer (pH 7.5), whereupon 1.25 g of N-cyclohexyl-N'-[2-(4-morpholinyl)-ethyl]-carbodiimide-methyl-p-toluene sulfonate is added in an icecold water-bath under constant stirring. The reaction mixture is stirred for 10 minutes whereupon 2.6 ml of a glucoamylase solution (120 mg/ml) are added and the pH of the reaction mixture is adjusted to 7.5. At 0°–4° C. the complete reaction time amounts to 48 hours and during this period the suspension is stirred twice for 6 hours each. At the beginning of the reaction the pH is controlled every half an hour and later once an hour and is adjusted, if necessary. The reaction having been completed the gel is separated by filtration and washed three times with 100 ml of a 0.1 molar potassium phosphate buffer each (pH 7.5), three times with 100 ml of a 0.1 molar potassium phosphate buffer comprising 1 mole of sodium chloride each (pH 7.5) and three times with 100 ml of a 0.1 molar potassium phosphate buffer each (pH 7.5). The gel is finally washed salt-free with distilled water and subjected to lyophilization. Thus 0.7 g of immobilized glucoamylase are obtained. Activity: 7.5 g of glucose are set free/hour/g xerogel.

EXAMPLE 16

0.5 g of Acrylex C-300 xerogel (binding capacity—i.e. —COOH content—7.33 m.equiv./g, particle size 40–120 μm) is suspended in 150 ml of a 0.1 molar potassium phosphate buffer (pH 7.5), whereupon 1.2 g of N-cyclohexyl-N'-[2-(4-morpholinyl)-ethyl]-carbodiimide-methyl-p-toluene sulfonate is added in an icecold water-bath under constant stirring. The reaction mixture is stirred for 10 minutes whereupon 2.55 ml of a glucoamylase solution (120 mg/ml) are added and the pH of the reaction mixture is adjusted to 7.5. At 0°–4° C. the complete reaction time amounts to 48 hours and during this period the suspension is stirred twice for 6 hours each. At the beginning of the reaction the pH is controlled every half an hour and later once an hour and is adjusted, if necessary. The reaction having been completed the gel is separated by filtration, and washed three times with 150 ml of a 0.1 molar potassium phosphate buffer each (pH 7.5), three times with 150 ml of a 0.1 molar potassium phosphate buffer comprising 1 mole of sodium chloride each (pH 7.5) and three times with 150 ml of a 0.1 molar potassium phosphate buffer each (pH 7.5). The gel is finally washed salt-free with distilled water and subjected to lyophilization. Thus 0.7 g of immobilized glucoamylase are obtained. Activity: 8.4 g of glucose are set free/hour/g xerogel.

TABLE 4

| | Immobilization of glucoamylase enzyme | | | |
| --- | --- | --- | --- | --- |
| Carrier | Immobilization activity (%) | Activity recovered in dissolved from (%) | Loss of activity (%) | Activity of the product /(unit/g xerogel) |
| Acrylex A | 0.7 | 39.0 | 60.3 | 1.6 |
| Acrylex C-100 | 4.3 | 45.3 | 50.4 | 5.7 |
| Acrylex C-200 | 1.6 | 59.0 | 39.4 | 7.5 |
| Acrylex C-300 | 1.8 | 69.5 | 28.7 | 8.4 |

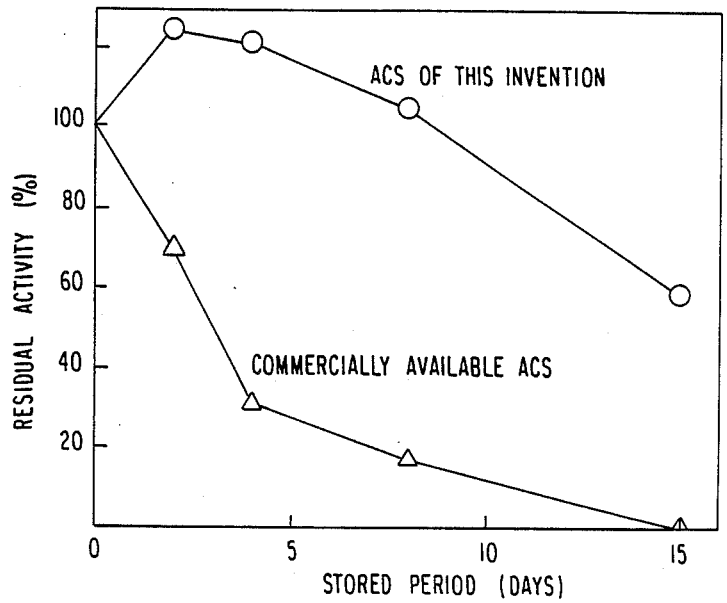

What we claim is:

1. A process for the preparation of an immobilized glucoamylase enzyme composition comprising:
    treating a glucoamylase enzyme with a carbodiimide compound which is water-soluble or soluble in an organic solvent at a temperature below 0° C.;
    mixing the treated glucoamylase and a polymer which is suspended and swollen in a buffer solution having a pH of from 4.5 to 9, said polymer being formed by polymerizing a monomer selected from the group consisting of N-aminoethyl-acrylamide, N-aminoethyl-methacrylamide, acrylamide, methacrylamide and mixtures thereof in the presence of a cross-linking agent selected from the group consisting of N,N'-methylene-bis-acrylic amide, ethylene diacrylate and N,N'-diallyl-tartaric amide, which polymers contain at least 1.0 m. equiv./g of —NH₂ functional groups;

stirring the mixture at 0° to 4° C. for a period of 24 to 72 hours to produce an immobilized glucoamylase enzyme composition;

filtering the immobilized glycoamylase enzyme composition produced; and thereafter washing the product composition several times with a buffer solution having a pH of 4.5 to 9 and then washing the product composition with water.

2. A process for the preparation of an immobilized glucoamylase enzyme composition comprising:

mixing a glucoamylase enzyme and a polymer which is suspended and swollen in a buffer solution having a pH of from 4.5 to 9, said polymer being formed by polymerizing a monomer selected from the group consisting of N-aminoethylacrylamide, N-aminoethyl-methacrylamide, acrylamide, methacrylamide and mixtures thereof in the presence of a cross-linking agent selected from the group consisting of N,N'-methylene-bis-acrylic amide, ethylene diacrylate and N,N'-diallyl-tartaric amide, which polymers contain at least 1.0 m. equiv./g of —NH₂ functional groups;

adding a carbodiimide compound which is water-soluble or soluble in an organic solvent at a temperature below 0° C. to the mixture thereby ensuring a controlled activation of the carboxy groups of the glycoamylase;

stirring the mixture at 0° to 4° C. for a period of 24 to 72 hours to produce an immobilized glucoamylase enzyme composition;

filtering the immobilized glycoamylase enzyme composition produced; and thereafter washing the product composition several times with a buffer solution having a pH of 4.5 to 9 and then washing the product composition with water.

3. A process for the preparation of an immobilized glucoamylase enzyme composition comprising:

treating a polymer which is suspended and swollen in a buffer solution having a pH of from 4.5 to 9, said polymer being formed by polymerizing a monomer selected from the group consisting of acrylic acid, methacrylic acid, acrylamide, methacrylamide and mixtures thereof in the presence of a cross-linking agent selected from the group consisting of N,N'-methylene-bis-acrylic amide, ethylene diacrylate and N,N'-diallyl-tartaric amide, which polymers contain at least 1.0 m. equiv./g of —COOH functional groups, with a carbodiimide compound which is water-soluble or soluble in an organic solvent at a temperature below 0° C. to form an activated carrier;

mixing a glycoamylase solution having a pH of 4.5 to 9 with the activated carrier;

stirring the mixture at 0° to 4° C. for a period of 24 to 72 hours to produce an immobilized glucoamylase enzyme composition;

filtering the immobilized glycoamylase enzyme composition produced; and thereafter washing the product composition several times with a buffer solution having a pH of 4.5 to 9 and then washing the product composition with water.

4. A process according to claim 1 or 2, wherein the polymer is an acrylamide-N,N'-methylene-bis-acrylamide-N-aminomethyl-acrylamide copolymer which has an exclusion molecular weight limit of at least 100,000 daltons.

5. A process according to claim 3, wherein the polymer is an acrylamide-N-N'-methylene-bis-acrylamide acrylic acid copolymer which has an exclusion molecular weight limit of at least 100,000 daltons.

6. A process according to any of claims 1 to 3, wherein the carbodiimide is N-cyclohexyl-N'-[2-(4-morpholinyl)-ethyl]-carbodiimide-methyl-p-toluenesulfonate or N-ethyl-N'-(3-dimethylaminopropyl)carbodiimide-hydrochloride.

7. A process according to any of claims 1 to 3 or 5, wherein a 0.1 molar potassium phosphate or sodium acetate solution is used as the buffer solution.

8. A process according to any of claims 1 to 3, wherein said period is 48 hours.

9. A process according to any of claims 1 to 3, wherein the product is subjected to lyophilization.

10. A process according to claim 6, wherein a 0.1 molar potassium phosphate or sodium acetate solution is used as the buffer solution.

11. A process according to claim 4, wherein a 0.1 molar potassium phosphate or sodium acetate solution is used as the buffer solution.

* * * * *

United States Patent [19]

Watanabe et al.

[11] Patent Number: 4,794,084

[45] Date of Patent: Dec. 27, 1988

[54] ACYL-COA SYNTHETASE

[75] Inventors: Mitsuo Watanabe; Hiromi Sato; Tomoko Kamei; Masao Kageyama, all of Kyoto, Japan

[73] Assignee: Unitika Ltd., Hyogo, Japan

[21] Appl. No.: 11,478

[22] Filed: Feb. 5, 1987

[30] Foreign Application Priority Data

Feb. 5, 1986 [JP] Japan .................................. 61-23084
Feb. 5, 1986 [JP] Japan .................................. 61-23085

[51] Int. Cl.$^4$ .......................... C12N 9/00; C12N 1/20
[52] U.S. Cl. ..................................... 435/183; 435/874; 435/253.3
[58] Field of Search ................. 435/183, 193, 253, 874

[56] References Cited

U.S. PATENT DOCUMENTS 4,269,942  5/1981  Yamada et al. ..................... 435/193
4,304,864  12/1981  Numa ................................... 435/193

FOREIGN PATENT DOCUMENTS 1005781  1/1986  Japan ................................... 435/193

Primary Examiner—Thomas G. Wiseman
Assistant Examiner—Charles L. Patterson, Jr.
Attorney, Agent, or Firm—Sughrue, Mion, Zinn, Macpeak, and Seas

[57] ABSTRACT

An acyl-CoA synthetase is disclosed having the following characteristics:

(a) Reaction:
  Capable of acting on saturated or unsaturated lower to higher fatty acids to produce a CoA derivative thereof (Acyl-CoA), adenosine monophosphate and pyrophosporic acid, in the presence of adenosine triphosphate and coenzyme A;

(b) Stability:
  Having a residual activity of not less than about 50% after being incubated in a buffer (pH about 7.5 for about 15 minutes at a temperature of about 55° C.; and (c) Optimum reaction temperature:
  Having an optimum reaction temperature in the range of from 50° to 60° C.

Also disclosed is Psuedomonas UKSW-3733 strain which is capable of producing the acyl-CoA synthetase, which has an optimum temperature for growth in the range of from 45° to 55° C. and is incapable of assimilating carbonates.

The acyl-CoA synthetase is highly stable and, therefore, can be used for preparation of clinical diagnosis kits capable of giving accurate test results over an extended period of time.

9 Claims, 4 Drawing Sheets